United States Patent
Joseph

(10) Patent No.: US 9,993,288 B2
(45) Date of Patent: Jun. 12, 2018

(54) FORCEPS

(71) Applicant: COVIDIEN LP, Mansfield, MA (US)

(72) Inventor: Daniel A. Joseph, Golden, CO (US)

(73) Assignee: COVIDIEN LP, Mansfield, MA (US)

( * ) Notice: Subject to any disclaimer, the term of this patent is extended or adjusted under 35 U.S.C. 154(b) by 381 days.

(21) Appl. No.: 14/721,075

(22) Filed: May 26, 2015

(65) Prior Publication Data

US 2015/0250526 A1    Sep. 10, 2015

Related U.S. Application Data

(63) Continuation of application No. 13/166,497, filed on Jun. 22, 2011, now Pat. No. 9,039,704.

(51) Int. Cl.
  *A61B 18/14* (2006.01)
  *A61B 17/28* (2006.01)
  (Continued)

(52) U.S. Cl.
  CPC ........ *A61B 18/1442* (2013.01); *A61B 17/285* (2013.01); *A61B 17/2812* (2013.01);
  (Continued)

(58) Field of Classification Search
  CPC ............. A61B 17/2812; A61B 17/285; A61B 17/3205; A61B 18/1442;
  (Continued)

(56) References Cited

U.S. PATENT DOCUMENTS

D249,549 S    9/1978 Pike
D263,020 S    2/1982 Rau, III
(Continued)

FOREIGN PATENT DOCUMENTS

CN    201299462    9/2009
DE    2415263 A1   10/1975
(Continued)

OTHER PUBLICATIONS

U.S. Appl. No. 12/769,444, filed Apr. 28, 2010, Glenn A. Norner.
(Continued)

*Primary Examiner* — Linda Dvorak
*Assistant Examiner* — Ryan T Clark

(57) ABSTRACT

A forceps includes first and second shaft members, each having a jaw member disposed at a distal end thereof. The first and second shaft members are pivotably coupled to one another toward the distal ends thereof and are moveable relative to one another between an open position and a closed position for moving the jaw members between a spaced-apart position and an approximated position. A knife assembly including a handle and a knife extending from the handle is also provided. The knife assembly is selectively translatable between a retracted position and an extended position, wherein the knife extends between the jaw members. The handle is disposed between the first and second shaft members and is configured to block further closure of the first and second shaft members beyond the closed position, thereby defining a minimum gap distance between the jaw members.

18 Claims, 6 Drawing Sheets

(51) Int. Cl.
*A61B 17/285* (2006.01)
*A61B 17/3205* (2006.01)
*A61B 18/00* (2006.01)
*A61B 17/00* (2006.01)

(52) U.S. Cl.
CPC ...... *A61B 17/3205* (2013.01); *A61B 18/1445* (2013.01); *A61B 2017/00438* (2013.01); *A61B 2018/0063* (2013.01); *A61B 2018/0094* (2013.01); *A61B 2018/00428* (2013.01); *A61B 2018/00607* (2013.01); *A61B 2018/1455* (2013.01)

(58) Field of Classification Search
CPC .. A61B 2018/00428; A61B 2018/1455; A61B 2017/00438; A61B 2018/00607
USPC .......................................................... 606/55
See application file for complete search history.

(56) References Cited

U.S. PATENT DOCUMENTS

| | | | |
|---|---|---|---|
| 4,452,246 A * | 6/1984 | Bader | A61B 17/0467 30/131 |
| D295,893 S | 5/1988 | Sharkany et al. | |
| D295,894 S | 5/1988 | Sharkany et al. | |
| D298,353 S | 11/1988 | Manno | |
| D299,413 S | 1/1989 | DeCarolis | |
| 5,219,354 A * | 6/1993 | Choudhury | A61B 17/0644 606/142 |
| D343,453 S | 1/1994 | Noda | |
| 5,275,613 A | 1/1994 | Haber et al. | |
| D348,930 S | 7/1994 | Olson | |
| D349,341 S | 8/1994 | Lichtman et al. | |
| D354,564 S | 1/1995 | Medema | |
| D358,887 S | 5/1995 | Feinberg | |
| D384,413 S | 9/1997 | Zlock et al. | |
| H1745 H | 4/1998 | Paraschac | |
| D402,028 S | 12/1998 | Grimm et al. | |
| D408,018 S | 4/1999 | McNaughton | |
| D416,089 S | 11/1999 | Barton et al. | |
| 6,010,516 A | 1/2000 | Hulka | |
| D424,694 S | 5/2000 | Tetzlaff et al. | |
| D425,201 S | 5/2000 | Tetzlaff et al. | |
| H1904 H | 10/2000 | Yates et al. | |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H2037 H | 7/2002 | Yates et al. | |
| D465,281 S | 11/2002 | Lang | |
| D466,209 S | 11/2002 | Bon | |
| 6,676,660 B2 | 1/2004 | Wampler et al. | |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| 7,041,102 B2 | 5/2006 | Truckai et al. | |
| D525,361 S | 7/2006 | Hushka | |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al. | |
| D545,432 S | 6/2007 | Watanabe | |
| D547,154 S | 7/2007 | Lee | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D582,038 S | 12/2008 | Swoyer et al. | |
| 7,513,898 B2 * | 4/2009 | Johnson | A61B 18/1445 606/171 |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| 7,922,718 B2 | 4/2011 | Moses et al. | |
| 7,955,331 B2 * | 6/2011 | Truckai | A61B 18/1442 606/50 |
| 7,955,332 B2 * | 6/2011 | Arts | A61B 17/2812 606/174 |
| 8,162,965 B2 * | 4/2012 | Reschke | A61B 17/285 606/167 |
| 9,039,704 B2 | 5/2015 | Joseph | |
| 2002/0107517 A1 * | 8/2002 | Witt | A61B 18/1442 606/50 |
| 2003/0009177 A1 | 1/2003 | Middleman et al. | |
| 2003/0114851 A1 * | 6/2003 | Truckai | A61B 18/1445 606/51 |
| 2005/0119655 A1 * | 6/2005 | Moses | A61B 18/1442 606/51 |
| 2005/0159745 A1 * | 7/2005 | Truckai | A61B 18/1442 606/51 |
| 2007/0106297 A1 * | 5/2007 | Dumbauld | A61B 18/1445 606/51 |
| 2008/0215048 A1 | 9/2008 | Hafner et al. | |
| 2009/0112246 A1 * | 4/2009 | Weisshaupt | A61B 17/285 606/174 |
| 2009/0125026 A1 | 5/2009 | Rioux et al. | |
| 2012/0083827 A1 * | 4/2012 | Artale | A61B 17/285 606/207 |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 10045375 C2 | 10/2002 |
| DE | 20 2007 009317 U1 | 8/2007 |
| DE | 202007009165 U1 | 8/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1159926 A3 | 3/2003 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-317934 A | 12/1996 |
| JP | 9-10223 C | 1/1997 |
| JP | 9-122138 A | 5/1997 |

(56) References Cited

FOREIGN PATENT DOCUMENTS

| | | | |
|---|---|---|---|
| JP | 10-155798 A | 6/1998 | |
| JP | 11-070124 A | 3/1999 | |
| JP | 11-169381 A | 6/1999 | |
| JP | 11-192238 A | 7/1999 | |
| JP | 11244298 A | 9/1999 | |
| JP | 2000-102545 A | 4/2000 | |
| JP | 2000342599 A | 12/2000 | |
| JP | 2000350732 A | 12/2000 | |
| JP | 2001-8944 | 1/2001 | |
| JP | 2001-29356 | 2/2001 | |
| JP | 2001128990 A | 5/2001 | |
| JP | 2001-190564 A | 7/2001 | |
| JP | 2004-517668 A | 6/2004 | |
| JP | 2004-528869 A | 9/2004 | |
| SU | 401367 A1 | 10/1973 | |
| WO | 0036986 A1 | 6/2000 | |
| WO | 0115614 A1 | 3/2001 | |
| WO | 0154604 A1 | 8/2001 | |
| WO | 2005/110264 A2 | 11/2005 | |

OTHER PUBLICATIONS

Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
U.S. Appl. No. 08/926,869, filed Sep. 10, 1997, James G. Chandler.
U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremeich.
U.S. Appl. No. 12/692,414, filed Jan. 22, 2010, Peter M. Mueller.
U.S. Appl. No. 12/696,592, filed Jan. 29, 2010, Jennifer S. Harper.
U.S. Appl. No. 12/696,857, filed Jan. 29, 2010, Edward M. Chojin.
U.S. Appl. No. 12/700,856, filed Feb. 5, 2010, James E. Krapohl.
U.S. Appl. No. 12/719,407, filed Mar. 8, 2010, Arlen J. Reschke.
U.S. Appl. No. 12/728,994, filed Mar. 22, 2010, Edward M. Chojin.
U.S. Appl. No. 12/748,028, filed Mar. 26, 2010, Jessica E.C. Olson.
U.S. Appl. No. 12/757,340, filed Apr. 9, 2010, Carine Hoarau.
U.S. Appl. No. 12/758,524, filed Apr. 12, 2010, Duane E. Kerr.
U.S. Appl. No. 12/759,551, filed Apr. 13, 2010, Glenn A. Homer.
U.S. Appl. No. 12/769,444, filed Apr. 28, 2010, Glenn A. Nomer.
U.S. Appl. No. 12/770,369, filed Apr. 29, 2010, Glenn A. Homer.
U.S. Appl. No. 12/770,380, filed Apr. 29, 2010, Glenn A. Homer.
U.S. Appl. No. 12/770,387, filed Apr. 29, 2010, Glenn A. Homer.
U.S. Appl. No. 12/773,526, filed May 4, 2010, Duane E. Kerr.
U.S. Appl. No. 12/773,644, filed May 4, 2010, Thomas J. Gerhardt.
U.S. Appl. No. 12/786,589, filed May 25, 2010, Duane E. Kerr.
U.S. Appl. No. 12/791,112, filed Jun. 1, 2010, David M. Garrison.
U.S. Appl. No. 12/792,001, filed Jun. 2, 2010, Duane E. Kerr.
U.S. Appl. No. 12/792,008, filed Jun. 2, 2010, Duane E. Kerr.
U.S. Appl. No. 12/792,019, filed Jun. 2, 2010, Duane E. Kerr.
U.S. Appl. No. 12/792,038, filed Jun. 2, 2010, Glenn A. Homer.
U.S. Appl. No. 12/792,051, filed Jun. 2, 2010, David M. Garrison.
U.S. Appl. No. 12/792,068, filed Jun. 2, 2010, Glenn A. Homer.
U.S. Appl. No. 12/792,097, filed Jun. 2, 2010, Duane E. Kerr.
U.S. Appl. No. 12/792,262, filed Jun. 2, 2010, Jeffrey M. Roy.
U.S. Appl. No. 12/792,299, filed Jun. 2, 2010, Jeffrey M. Roy.
U.S. Appl. No. 12/792,330, filed Jun. 2, 2010, David M. Garrison.
U.S. Appl. No. 12/822,024, filed Jun. 23, 2010, Peter M. Mueller.
U.S. Appl. No. 12/821,253, filed Jun. 23, 2010, Edward M. Chojin.
U.S. Appl. No. 12/832,772, filed Jul. 8, 2010, Gary M. Couture.
U.S. Appl. No. 12/843,384, filed Jul. 26, 2010, David M. Garrison.
U.S. Appl. No. 12/845,203, filed Jul. 28, 2010, Gary M. Couture.
U.S. Appl. No. 12/853,896, filed Aug. 10, 2010, William H. Nau, Jr.
U.S. Appl. No. 12/859,896, filed Aug. 20, 2010, Peter M. Mueller.
U.S. Appl. No. 12/861,198, filed Aug. 23, 2010, James a. Gilbert.
U.S. Appl. No. 12/861,209, filed Aug. 23, 2010, William H. Nau, Jr.
U.S. Appl. No. 12/876,668, filed Sep. 7, 2010, Sara E. Anderson.
U.S. Appl. No. 12/876,680, filed Sep. 7, 2010, Peter M. Mueller.
U.S. Appl. No. 12/876,705, filed Sep. 7, 2010, Kristin D. Johnson.
U.S. Appl. No. 12/876,731, filed Sep. 7, 2010, Kristin D. Johnson.
U.S. Appl. No. 12/877,199, filed Sep. 8, 2010, Arlen J. Reschke.
U.S. Appl. No. 12/877,482, filed Sep. 8, 2010, Gary M. Couture.
U.S. Appl. No. 12/895,020, filed Sep. 30, 2010, Jeffrey M. Roy.
U.S. Appl. No. 12/896,100, filed Oct. 1, 2010, Ryan Artale.
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12:876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.

(56) References Cited

OTHER PUBLICATIONS

Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report Ep 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 185386.9 dated Jan. 10, 2011.
Int'l Search Report EP 10 185405.7 dated Jan. 5, 2011.
Int'l Search Report EP 10 157500.9 dated Jul. 30, 2010.
Int'l Search Report EP 10 159205.3 dated Jul. 7, 2010.
Int'l Search Report EP 10 160870,1 dated Aug. 9, 2010.
Int'l Search Report EP 10 161596.1 dated Jul. 28, 2010.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182022.3 dated Mar. 11, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 161117.4 dated Jun. 30, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.

(56) References Cited

OTHER PUBLICATIONS

Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
U.S. Appl. No. 12/897,346, filed Oct. 4, 2010, Ryan Artale.
U.S. Appl. No. 12/906,672, filed Oct. 18, 2010, Kathy E. Rooks.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/947,420, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, Iv.
U.S. Appl. No. 12/981,787, filed Dec. 30, 2010, John R. Twomey.
U.S. Appl. No. 13/006,538, filed Jan. 14, 2011, John W. Twomey.
U.S. Appl. No. 13/029,390, filed Feb. 17, 2011, Michael C. Moses.
U.S. Appl. No. 13/030,231, filed Feb. 18, 2011, Jeffrey M. Roy.
U.S. Appl. No. 13/050,182, filed Mar. 17, 2011, Glenn A. Homer.
U.S. Appl. No. 13/072,945, filed Mar. 28, 2011, Patrick L. Dumbauld.
U.S. Appl. No. 13/075,847, filed Mar. 30, 2011, Gary M. Couture.
U.S. Appl. No. 13/080,383, filed Apr. 5, 2011, David M. Garrison.
U.S. Appl. No. 13/083,962, filed Apr. 11, 2011, Michael C. Moses.
U.S. Appl. No. 13/085,144, filed Apr. 12, 2011, Keir Hart.
U.S. Appl. No. 13/089,779, filed Apr. 19, 2011, Yevgeniy Fedotov.
U.S. Appl. No. 13/091,331, filed Apr. 21, 2011, Jeffrey R. Townsend.
U.S. Appl. No. 13/102,573, filed May 6, 2011, John R. Twomey.
U.S. Appl. No. 13/102,604, filed May 6, 2011, Paul E. Ourada.
U.S. Appl. No. 13/108,093, filed May 16, 2011, Boris Chernov.
U.S. Appl. No. 13/108,129, filed May 16, 2011, Boris Chernov.
U.S. Appl. No. 13/108,152, filed May 16, 2011, Boris Chernov.
U.S. Appl. No. 13/108,177, filed May 16, 2011, Boris Chernov.
U.S. Appl. No. 13/108,196, filed May 16, 2011, Boris Chernov.
U.S. Appl. No. 13/108,441, filed May 16, 2011, Boris Chernov.
U.S. Appl. No. 13/108,468, filed May 16, 2011, Boris Chernov.
U.S. Appl. No. 13/111,642, filed May 19, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.
U.S. Appl. No. 13/166,497, filed Jun. 22, 2011, Daniel A. Joseph.
U.S. Appl. No. 13/179,919, filed Jul. 11, 2011, Russell D. Hempstead.
U.S. Appl. No. 13/179,960, filed Jul. 11, 2011, Boris Chernov.
U.S. Appl. No. 13/179,975, filed Jul. 11, 2011, Grant T. Sims.
U.S. Appl. No. 13/180,018, filed Jul. 11, 2011, Chase Collings.
U.S. Appl. No. 13/183,856, filed Jul. 15, 2011, John R. Twomey.
U.S. Appl. No. 13/185,593, filed Jul. 19, 2011, James D. Allen, IV.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).

* cited by examiner

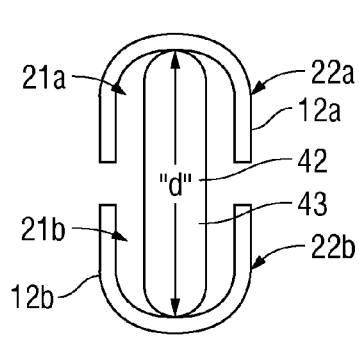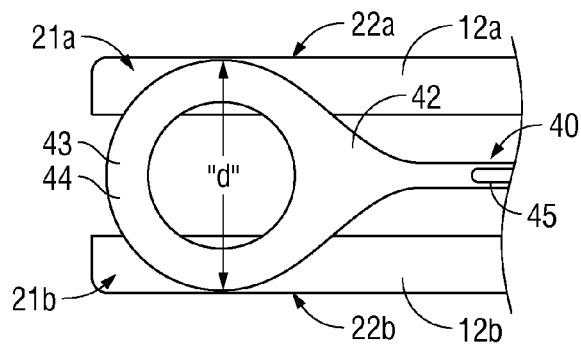
FIG. 5A  FIG. 5B
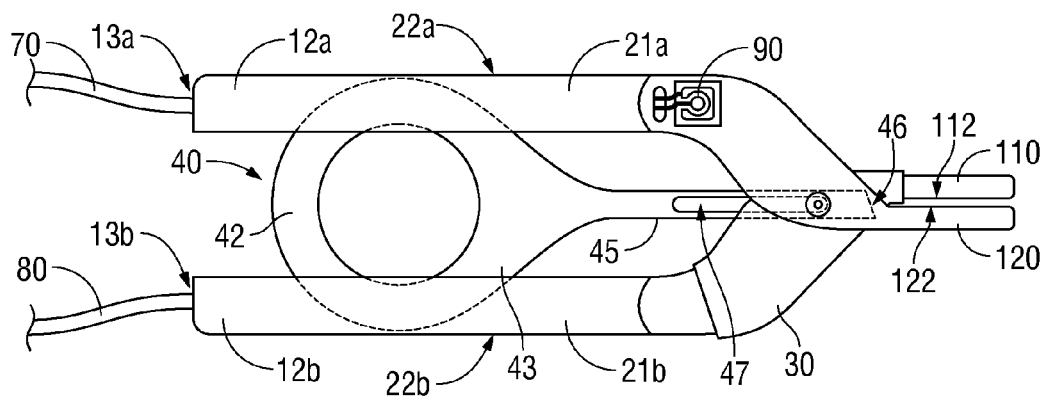
FIG. 6A
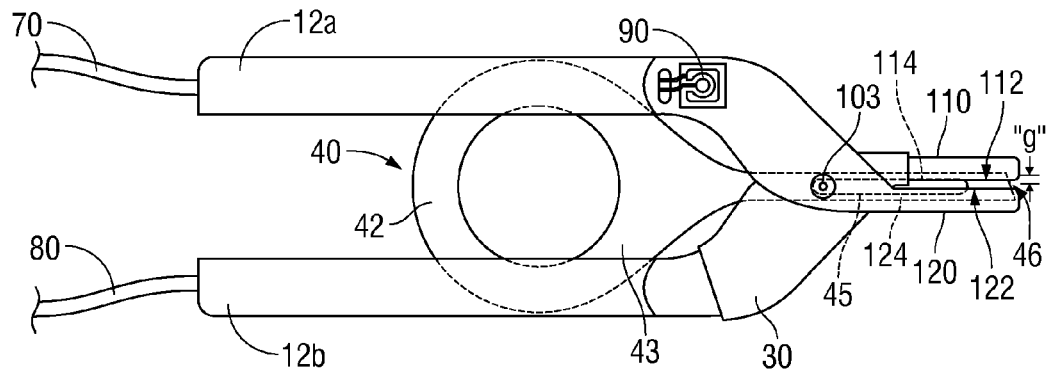
FIG. 6B

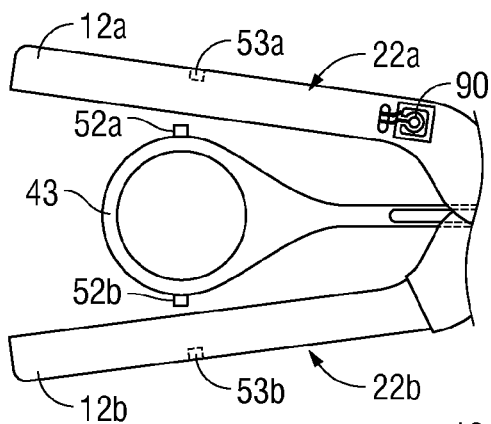
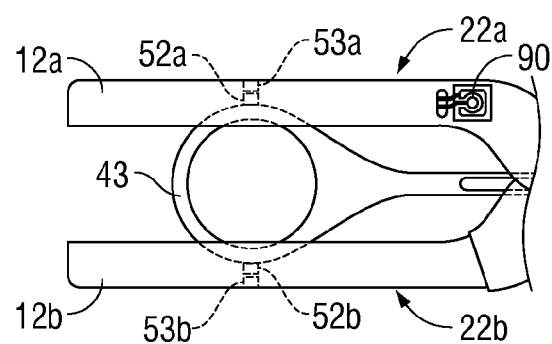
FIG. 8A
FIG. 8B
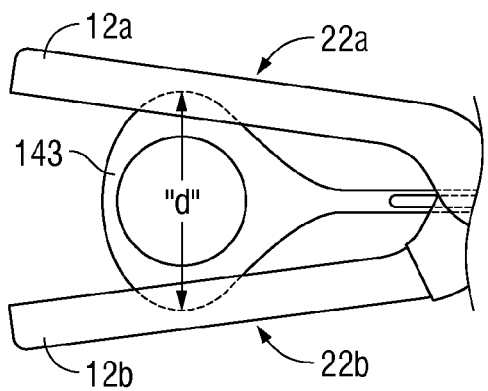
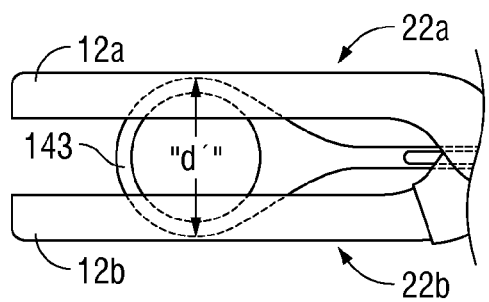
FIG. 9A
FIG. 9B

FORCEPS

CROSS-REFERENCE TO RELATED APPLICATIONS

This present application is a continuation application of U.S. patent application Ser. No. 13/166,497, filed on Jun. 22, 2011, the entire contents of which are hereby incorporated by reference herein.

BACKGROUND

The present disclosure relates to a forceps and, more particularly, to a surgical forceps for sealing and/or dividing tissue.

TECHNICAL FIELD

A forceps is a plier-like instrument which relies on mechanical action between its jaws to grasp, clamp and constrict vessels or tissue. Electrosurgical forceps utilize both mechanical clamping action and electrical energy to affect hemostasis by heating tissue and blood vessels to coagulate and/or cauterize tissue. Certain surgical procedures require more than simply cauterizing tissue and rely on the unique combination of clamping pressure, precise electrosurgical energy control and gap distance (i.e., distance between opposing jaw members when closed about tissue) to "seal" tissue, vessels and certain vascular bundles.

Typically, once a vessel is sealed, the surgeon has to accurately sever the vessel along the newly formed tissue seal. Accordingly, many vessel sealing instruments have been designed which incorporate a knife or blade member which effectively severs the tissue after forming a tissue seal.

SUMMARY

In accordance with one embodiment of the present disclosure, a forceps is provided. The forceps includes first and second shaft members and a knife assembly. Each of the first and second shaft members includes a jaw member disposed at a distal end thereof. The first and second shaft members are pivotably coupled to one another toward the distal ends thereof. One (or both) of the first and second shaft members is moveable relative to the other between an open position and a closed position for moving the jaw members between a spaced-apart position and an approximated position. The knife assembly includes a handle and a knife extending from the handle. The knife assembly is selectively translatable, relative to the shaft members, between a retracted position and an extended position. In the extended position, the knife extends between the jaw members. The handle is disposed between the first and second shaft members and is configured to block further closure of the first and second shaft members beyond the closed position, thereby defining a minimum gap distance between the jaw members.

In one embodiment, the minimum gap distance between the jaw members is in the range of about 0.001 inches to about 0.006 inches.

In another embodiment, each shaft member and its respective jaw member is monolithically formed as a single component.

In another embodiment, one or both of the jaw members is adapted to connect to a source of electrosurgical energy.

In still another embodiment, the handle of the knife assembly defines a finger ring configured to facilitate translation of the knife assembly between the retracted position and the extended position.

In yet another embodiment, one or both of the jaw members includes a longitudinally-extending knife channel defined therein. The longitudinally-extending knife channel is configured to permit reciprocation of the knife therethrough.

In still yet another embodiment, the knife includes a longitudinal slot defined therein. The longitudinal slot of the knife is configured to receive a pivot pin therethrough upon which the first and second shaft members are pivotably coupled. The pivot pin is configured to translate longitudinally along the slot as the knife assembly is translated between the retracted position and the extended position.

Another embodiment of a forceps provided in accordance with the present disclosure includes first and second shaft members and a knife assembly. Each of the first and second shaft members includes a jaw member disposed at a distal end thereof. The first and second shaft members are pivotably coupled to one another toward the distal ends thereof and one or both of the shaft members is moveable relative to the other between an open position and a closed position for moving the jaw members between a spaced-apart position and an approximated position. The knife assembly includes a handle and a knife extending from the handle. The knife assembly is selectively translatable between a retracted position and an extended position. In the extended position, the knife extends between the jaw members. The handle is disposed between the first and second shaft members. More specifically, a portion of the (or the entire) handle is disposed within a guide track defined within one or both of the shaft members. The guide track is configured to guide translation of the knife assembly between the retracted position and the extended position.

In one embodiment, one or both of the shaft members includes a longitudinal trough defined therein. The longitudinal trough forms the guide track for guiding translation of the knife assembly between the retracted position and the extended position.

In another embodiment, the handle of the knife assembly and the guide track define complementary transverse, cross-sectional configurations to facilitate translation of the knife assembly between the retracted position and the extended position.

In another embodiment, the handle of the knife assembly defines a finger ring configured to facilitate translation of the knife assembly between the retracted position and the extended position.

In still another embodiment, each shaft member and its respective jaw member are monolithically formed as a single component.

In yet another embodiment, one or both of the jaw members is adapted to connect to a source of electrosurgical energy.

In still yet another embodiment, one or both of the jaw members includes a longitudinally-extending knife channel defined therein. The longitudinally-extending knife channel is configured to permit reciprocation of the knife therethrough.

A forceps in accordance with another embodiment of the present disclosure is provided including first and second shaft members and a knife assembly. Each shaft member has a jaw member disposed at a distal end thereof. The shaft members are pivotably coupled to one another toward the distal ends thereof and one or both of the shaft members is moveable relative to the other between an open position and a closed position for moving the jaw members between a spaced-apart position and an approximated position. The knife assembly includes a handle and a knife extending from the handle. The knife assembly is selectively translatable between a retracted position and an extended position. In the extended position, the knife extends between the jaw members. One or both of the shaft members includes a guide track for guiding translation of the knife assembly between the retracted and extended positions. The handle of the knife assembly is disposed between the first and second shaft members and is configured to define a minimum gap distance between the jaw members when the jaw members are disposed in the approximated position.

In one embodiment, one or both of the jaw members is adapted to connect to a source of electrosurgical energy.

In another embodiment, the minimum gap distance between the jaw members is in the range of about 0.001 inches to about 0.006 inches.

In another embodiment, one or both of the jaw members includes a longitudinally-extending knife channel defined therein. The longitudinally-extending knife channel is configured to permit reciprocation of the knife therethrough.

In still another embodiment, the handle of the knife assembly and the guide track define complementary transverse, cross-sectional configurations to facilitate translation of the knife assembly between the retracted position and the extended position.

In yet another embodiment, the handle of the knife assembly defines a finger ring configured to facilitate translation of the knife assembly between the retracted position and the extended position.

BRIEF DESCRIPTION OF THE DRAWINGS

Various embodiments of the present disclosure are described herein with reference to the drawings wherein:

FIG. 5A is a transverse, cross-sectional view of a handle portion of the forceps of FIG. 1;

FIG. 5B is a longitudinal, cross-sectional view of the handle portion of the forceps of FIG. 1;

FIG. 6A is a side view of the forceps of FIG. 1 wherein a knife assembly is disposed in a retracted position;

FIG. 6B is a side view of the forceps of FIG. 1 wherein the knife assembly is disposed in an extended position;

FIG. 8A is a side view of another embodiment of a forceps provided in accordance with the present disclosure wherein the shaft members are disposed in the open position;

FIG. 8B is a side view of the forceps of FIG. 8A wherein the shaft members are disposed in the closed position;

FIG. 9A is a side view of still another embodiment of a forceps provided in accordance with the present disclosure wherein the shaft members are disposed in the open position; and FIG. 9B is a side view of the forceps of FIG. 9A wherein the shaft members are disposed in the closed position.

DETAILED DESCRIPTION

Figure 1:
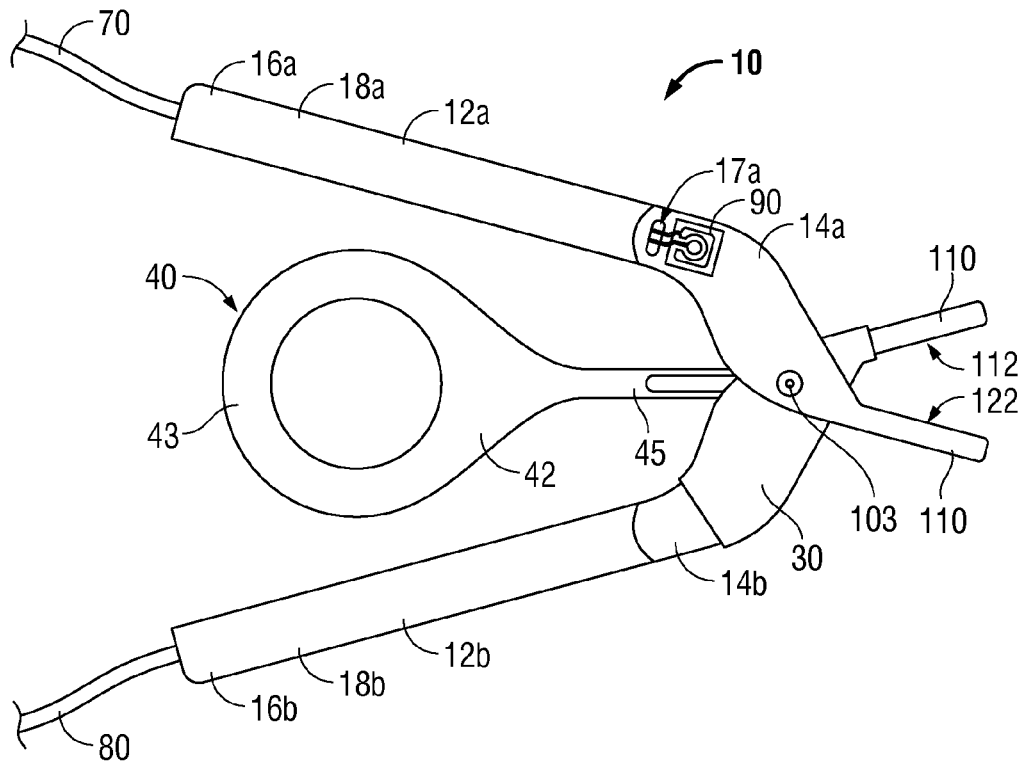
FIG. 1 is a side view of a forceps according to one embodiment of the present disclosure wherein jaw members of the forceps are disposed in a spaced-apart position.

Embodiments of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

Turning now to FIGS. 1-4, a forceps provided in accordance with the present disclosure is shown generally identified by reference numeral 10. Forceps 10 includes two shaft members 12a, 12b, each including a distal end 14a, 14b and a proximal end 16a, 16b, respectively. Each shaft member 12a, 12b further includes a jaw member 120, 110 disposed at the respective distal end 14a, 14b thereof. Shaft members 12a, 12b are pivotably coupled to one another about pivot 103 towards distal ends 14a, 14b, respectively, thereof such that shaft members 12a and 12b are moveable relative to one another from an open position (FIG. 1), wherein jaw members 110 and 120 are disposed in spaced-apart relation relative to one another, to a closed position (FIG. 2), wherein jaw members 110 and 120 are pivoted to an approximated position to grasp tissue therebetween.

Each shaft member 12a, 12b, including respective jaw members 120, 110, is monolithically formed, e.g., as a single component. Shaft members 12a, 12b may be formed via stamping, or via any other suitable method, e.g., casting, molding, etc. Shaft members 12a, 12b are formed from an electrically conductive material, e.g., a metal, such that jaw members 110, 120 each define an opposed tissue sealing surface 112, 122, respectively, that, as will be described in greater detail below, is adapted to connect to a source of electrical energy (not explicitly shown) for sealing tissue grasped between jaw members 110, 120. Further, a longitudinally-extending knife channel 114, 124, may be defined within one or both of jaw members 110, 120, respectively, to permit reciprocation of a knife bar 45 therethrough to cut the previously sealed tissue.

Figure 2:
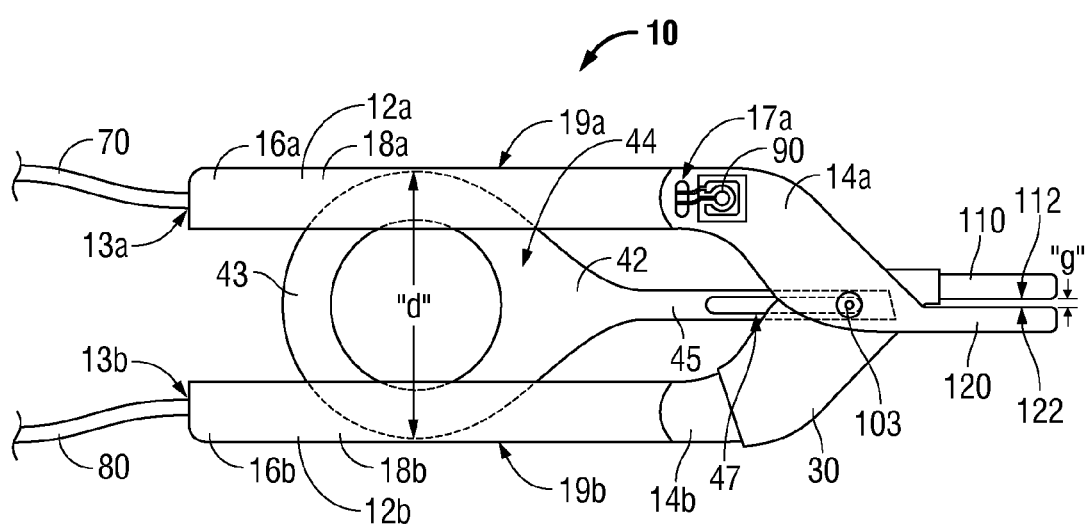
FIG. 2 is a side view of the forceps of FIG. 1 wherein the jaw members are disposed in an approximated position.
Figure 3:
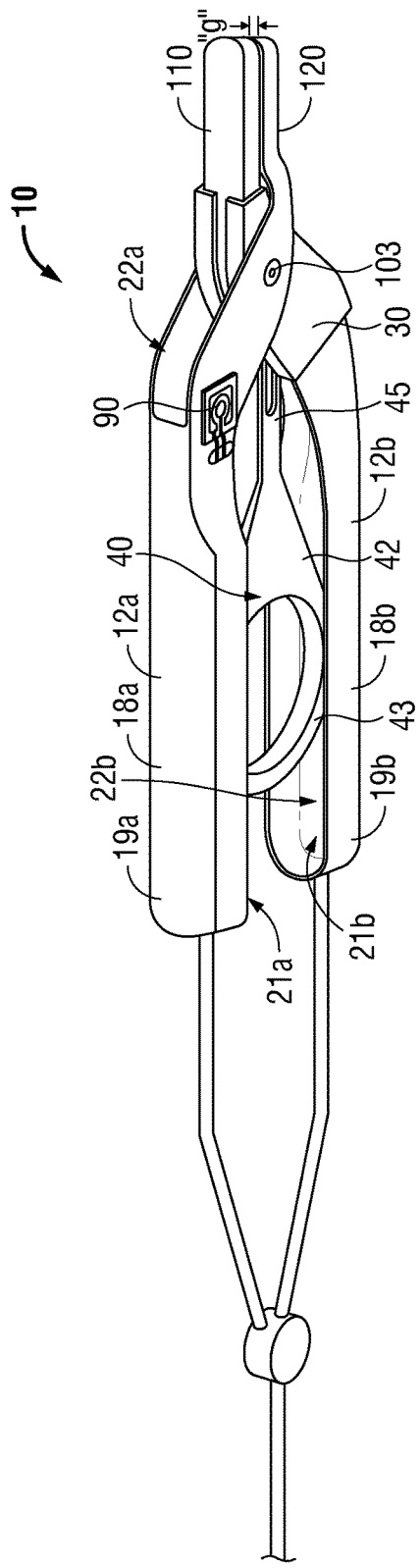
FIG. 3 is a side, perspective view of the forceps of FIG. 1.

Referring still to FIGS. 1-4, each shaft member 12a, 12b of forceps 10 defines a handle portion 18a, 18b toward a proximal end 16a, 16b, respectively, thereof and, as mentioned above, includes respective jaw members 120, 110 disposed at distal ends 14a, 14b, respectively, thereof. Further, shaft member 12a defines a bifurcated configuration toward a distal end 14a thereof such that, as best shown in FIG. 3, shaft member 12b may pass between the bifurcated portion of shaft member 12a adjacent pivot 103. An insulative sleeve 30 is disposed about shaft member 12b adjacent pivot 103 to inhibit contact between shaft members 12a, 12b as shaft member 12b passes between shaft member 12a. As can be appreciated, insulative sleeve 30 maintains electrical isolation between shaft members 12a, 12b.

With continued reference to FIGS. 1-4, handle portions 18a, 18b of shaft members 12a, 12b, respectively, define substantially hollow configurations. More specifically, handle portions 18a, 18b of shaft members 12a, 12b, respectively, define opposed U-shaped configurations having hollow interior troughs 21a, 21b, respectively. As will be described in greater detail below, hollow interior troughs 21a, 21b, respectively, of handle portions 18a, 18b, respectively, define respective longitudinal tracks 22a, 22b configured to guide the translation of knife assembly 40 therethrough.

Each handle portion 18a, 18b further includes an electrically-insulative coating, or covering 19a, 19b, respectively, disposed thereon. More specifically, handle portions 18a, 18b may be dip coated with an insulative material, may include a form-fitted insulative jacket disposed thereabout, or may be otherwise configured to include an insulating outer layer disposed about a substantial portion thereof. As can be appreciated, electrically-insulative coverings 19a, 19b permit the user to grasps shaft members 12a, 12b of forceps 10 without the need for insulative gloves (not shown) or other specialized equipment.

With continued reference to FIGS. 1-4, forceps 10 further includes a knife assembly 40 operably coupled between shaft members 12a, 12b. Knife assembly 40 includes a handle portion 42 having a finger ring 43 and a knife bar 45 extending distally from handle portion 42 to define a cutting distal end 46. Handle portion 42, similar to handle portions 18a, 18b of shaft members 12a, 12b, respectively, may include an insulative coating, or covering 44 disposed thereabout, allowing the user to grasp finger ring 43 without the need for additional protection. Alternatively, handle portion 42 of knife assembly 40 may be formed from plastic and may be molded to the metal knife bar 45. Knife bar 45 includes a longitudinally-extending slot 47 defined therein configured to permit reciprocation of knife bar 45 relative to pivot 103. More particularly, pivot 103 is disposed through slot 47 to permit knife assembly 40 to be moved relative to jaw members 110, 120 between a retracted position (FIG. 6A) and an extended position (FIG. 6B). Various configurations of knife bar 45 will be described in greater detail hereinbelow with reference to FIGS. 7A-7D.

Finger ring 43 of handle portion 42 of knife assembly 40, as shown in FIGS. 1-4, is disposed within troughs 21a, 21b of U-shaped hollow shaft members 12a, 12b, respectively, and may be configured to set a gap distance "g" between jaw members 110, 120 when jaw members 110, 120 are moved to the approximated position. More specifically, finger ring 43 is positioned between shaft members 12a, 12b and defines a sufficient outer diameter "d" to inhibit shaft members 12a, 12b from being moved beyond the closed position wherein tissue sealing surfaces 112, 122 of respective jaw members 110, 120 are in contact with one another. In other words, finger ring 43 physically inhibits further closure of shaft members 12a, 12b, e.g., since finger ring 43 is disposed therebetween, thereby defining a minimum gap distance "g" between jaw members 110, 120 corresponding to the position wherein shaft members 12a, 12b can no longer be further closed relative to one another. As can be appreciated, the specific outer diameter "d" of finger ring 43 may be provided in accordance with the desired gap distance "g" between jaw members 110, 120 when jaw members 110, 120 are disposed in the approximated position. Further, finger ring 43 may include diameter-enlarging attachments (not shown), or other features configured to increase the relative outer diameter "d" of finger ring 43 to thereby increase the gap distance "g" between jaw members 110, 120 for use with various compositions and sizes of tissue to be sealed. The gap distance "g" between sealing surfaces 112, 122 of jaw members 110, 120, respectively, during sealing of tissue grasped therebetween may be in the range of about 0.001 inches to about 0.006 inches.

Referring now to FIGS. 5A-5B and 6A-6B, finger ring 43 is further configured to guide knife assembly 40 as knife assembly 40 is translated between the retracted position (FIG. 6A) and the extended position (FIG. 6B) to cut tissue grasped between sealing surfaces 112, 122 of jaw members 110, 120, respectively. More specifically, as mentioned above, opposed U-shaped troughs 21a, 21b of respective handle portions 18a, 18b of shaft members 12a, 12b, respectively, are shaped to define respective longitudinal tracks 22a, 22b. Longitudinal tracks 22a, 22b guide finger ring 43, on either side thereof as finger ring 43 is translated between the retracted position and the extended position, thereby helping to maintain a substantially straight blade path as knife bar 45 is translated through knife channels 114, 124 defined within jaw members 110, 120, respectively. As can be appreciated, U-shaped troughs 21a, 21b of handle portions 18a, 18b of shaft members 12a, 12b, respectively, inhibit eccentric translation of knife assembly 40 by substantially confining finger ring 43 to longitudinal movement along tracks 22a, 22b of shaft members 12a, 12b, respectively. As best shown in FIG. 5A, longitudinal tracks 22a, 22b and finger ring 43 of handle portion 42 of knife assembly 40 may define complementary transverse, cross-sectional configurations to facilitate relatively smooth and translation of knife assembly 40 between the retracted and extended positions.

As shown in FIGS. 2-3, and as mentioned above, shaft member 12a and/or shaft member 12b is adapted to connect to a source of electrical energy (not explicitly shown) for energizing sealing surfaces 112, 122 of jaw members 110, 120, respectively, to seal tissue grasped therebetween. More particularly, wires 70, 80 are coupled to the source of energy (not explicitly shown) at one end. Each wire 70, 80 extends through a respective proximal aperture 13a, 13b defined within handle portions 18a, 18b of shaft members 12a, 12b, respectively. Wire 80, e.g., the negative, or return wire 80, is coupled directly to the electrically-conductive surface of shaft member 12b, e.g., a portion of shaft member 12b that is not covered by insulative coating 30, toward proximal end 16b thereof. Wire 70, e.g., the positive, or supply wire 70, on the other hand, extends distally along shaft member 12a and through a slot 17a defined within shaft member 12a towards distal end 14a thereof. This configuration may also be reversed, e.g., where the return wire 80 is coupled to shaft member 12a and the supply wire 70 is coupled to shaft member 12b, or any other suitable configuration for coupling electrical energy to shaft member 12a and/or 12b may be provided. Alternatively, forceps 10 may be configured as a monopolar device.

With continued reference to FIGS. 2-3, wire 70 is coupled to shaft member 12a via an actuator 90, allowing the user to selectively supply electrical energy to shaft members 12a, 12b and, thus, to sealing surfaces 122, 112 of jaw members 120, 110, respectively, due to the electrically conductive configuration of shaft members 12a, 12b. The construction of shaft members 12a, 12b entirely from a conductive material also provides a larger surface area for heat dissipation during the tissue sealing process.

Any suitable actuator 90 for controlling the supply of electrical energy to sealing surfaces 112, 122 of members 110, 120, respectively, may be provided.

Figure 4:
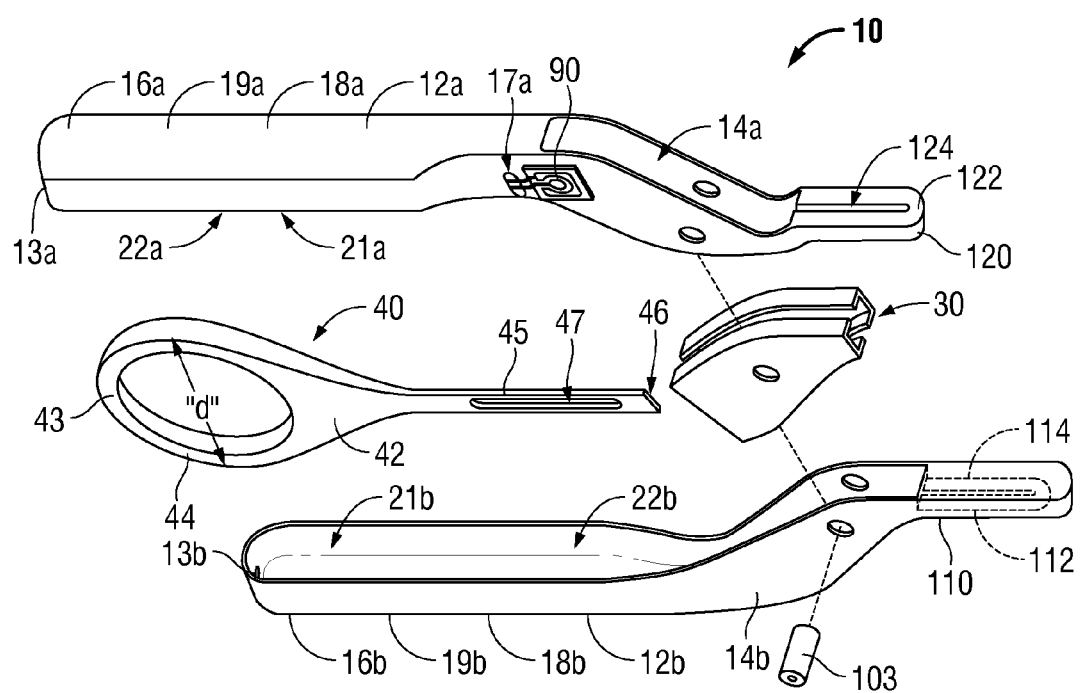
FIG. 4 is a side, exploded perspective view of the forceps of FIG. 1 shown with parts separated.
Figure 7A:
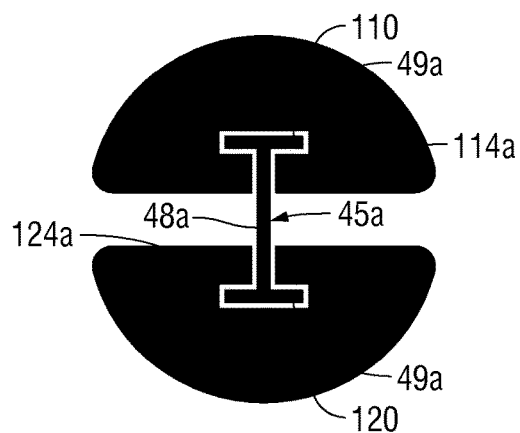
FIG. 7A is a transverse, cross-sectional view of one embodiment of jaw members configured for use with the forceps of FIG. 1.

Referring now to FIGS. 7A-7D, in conjunction with FIG. 4, various configurations of the knife bar 45 of knife assembly 40 and corresponding knife channels 114, 124, defined within jaw members 110, 120, respectively, will be described. As shown in FIG. 7A, knife bar 45a defines a generally "I"-shaped configuration and blade channels 114a, 124a correspondingly define complementary configurations to permit reciprocation of "I"-shaped knife bar 45a therethrough. The body portion 48a of "I"-shaped knife bar 45 may be formed from a metal, e.g., via stamping, while the first and second flanges 49a of knife bar 45a may be formed from a plastic. The plastic flanges 49a may be molded or otherwise coupled to body portion 48a of knife bar 45a at the opposed ends thereof. Alternatively, the entire knife bar 45a may be formed from metal.

Figure 7B:
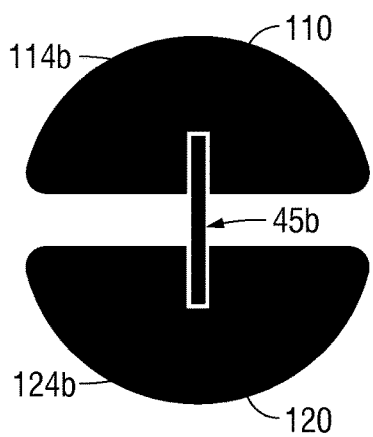
FIG. 7B is a transverse, cross-sectional view of another embodiment of jaw members configured for use with the forceps of FIG. 1.

FIG. 7B shows another configuration wherein knife bar 45b defines a linear configuration and blade channels 114b, 124b each define similar configurations for reciprocation of knife bar 45b therethrough.

Figure 7C:
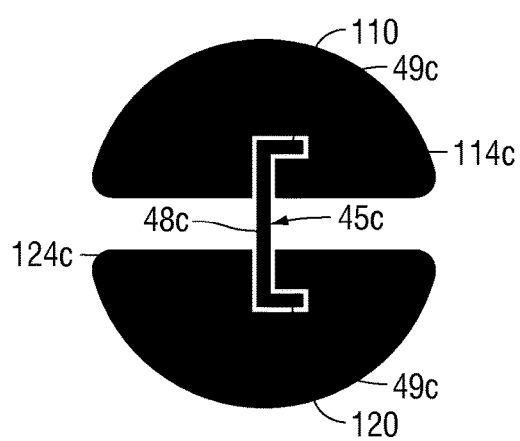
FIG. 7C is a transverse, cross-sectional view of still another embodiment of jaw members configured for use with the forceps of FIG. 1.

FIG. 7C shows yet another configuration of a knife bar 45c and corresponding knife channels 114c, 124c that is similar to knife bar 45a and knife channels 114a, 124a of FIG. 7A, except that flanges 49c of knife bar 45c extend in only one direction from knife body 48c. However, flanges 49c of knife bar 45c may alternatively be configured to extend in opposite directions. Knife channels 114c, 124c of jaw members 110, 120, respectively, as can be appreciated, are formed complementarily to the configuration of knife bar 45c. As in the embodiment of FIG. 7A, flanges 49c may be formed from plastic, or other suitable material, and may be molded to the metal body portion 48c of knife bar 45c, or may be monolithically formed with body portion 48c as a single component.

Figure 7D:
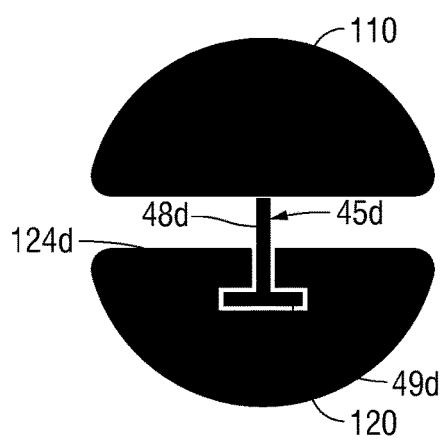
FIG. 7D is a transverse, cross-sectional view of yet another embodiment of jaw members configured for use with the forceps of FIG. 1.

FIG. 7D shows still another configuration of a knife bar 45d and corresponding knife channel 124d similar to knife bar 45a and knife channels 114a, 124a of FIG. 7A, except that only one of jaw members 110, 120, e.g., jaw member 120, includes a knife channel 124d defined therein. However, this configuration may be reversed, e.g., where only jaw member 110 includes the knife channel defined therein. Flange 49d of knife bar 45d may be formed from plastic, or other suitable material, and knife body 48d may be formed from metal, as discussed above. Other configurations of the knife bar 45 and the corresponding knife channel(s) 114, 124 similar to those described about with reference to FIGS. 7A-7D may also be provided.

The use and operation of forceps 10 will now be described with reference to FIGS. 1-2 and 6A-6B. Initially, as shown in FIG. 1, with shaft members 12a, 12b disposed in the open position and, thus, with jaw members 110, 120 disposed in the spaced-apart position, forceps 10 is moved into position such that tissue to be grasped, sealed and divided is disposed between sealing surfaces 112, 122 of jaw members 110, 120, respectively. In this position, knife assembly 40 is disposed in the retracted position, wherein knife bar 45 is positioned proximally of jaw members 110, 120, e.g., such that distal cutting edge 46 of knife bar 45 does not extend between jaw members 110, 120.

Once forceps 10 is positioned as desired, the user may grasp handle portions 18a, 18b of shaft members 12a, 12b, respectively, and squeeze shaft members 12a, 12b towards the closed position, as best shown in FIG. 2, thereby pivoting jaw members 110, 120 toward the approximated position to grasp tissue therebetween. More specifically, shaft members 12a, 12b are moved toward one another until shaft members 12a, 12b each contact opposed sides of finger ring 43 of knife assembly 40, which blocks, or inhibits further closure of shaft members 12a, 12b. This position corresponds to the closed position of shaft members 12a, 12b and, thus, the approximated position of jaw members 110, 120. This closed position is regulated to assume a consistent closure pressure between jaw members 110, 120 to effect a quality tissue seal. Typically, the closure pressure between jaw members 110, 120 is in the range from about 3 kg/cm$^2$ to about 16 kg/cm$^2$. Further, as mentioned above, finger ring 43 is configured such that a minimum gap distance "g" is defined between sealing surfaces 112, 122 of jaw members 110, 120, respectively, when jaw members 110, 120 are moved to the approximated position. The user may maintain jaw members 110, 120 in this approximated position grasping tissue therebetween simply by maintaining shaft members 12a, 12b in contact with finger ring 43 of knife assembly 40, e.g., by retaining shaft members 12a, 12b in the closed position abutting finger ring 43 of knife assembly 40. At this point, knife assembly 40 remains disposed in the retracted position (see FIG. 6A).

With jaw members 110, 120 disposed in the closed position grasping tissue therebetween, electrical energy may be supplied to sealing surfaces 112, 122 of jaw members 110, 120, respectively, to conduct energy through tissue grasped between jaw members 110, 120 to effect a tissue seal. More particularly, the user may depress, or otherwise activate actuator 90 to supply electrical energy to shaft member 12a and/or shaft member 12b. Since each shaft member 12a, 12b, including jaw members 120, 110 and sealing surfaces 122, 112, respectively, is formed form a conductive material, the energy supplied to shaft member 12a and/or shaft member 12b energizes sealing surfaces 122, 112 such that energy is conducted therebetween and through tissue to effect a tissue seal. As discussed above, the gap distance "g" between sealing surfaces 112, 122, which is defined by finger ring 43, and regulating the closure pressure between jaw members 110, 120, helps ensure formation of an adequate tissue seal. Further, as mentioned above, during tissue sealing, heat is dissipated throughout shaft members 12a and 12b, which provide a relatively large surface area for heat dissipation, thereby reducing the overall heating of shaft members 12a, 12b. Insulative coatings 19a, 19b disposed about handle portions 18a, 18b of shaft members 12a, 12b help protect the user from directly contacting the heated shaft members 12a, 12b.

Referring to FIGS. 8A-8B, finger ring 43 may also include one or more contacts 52a, 52b that are configured to engage corresponding contact(s) 53a, 53b disposed within track 22a and/or track 22b of shaft members 12a, 12b, respectively, to close an electrical circuit upon movement of shaft members 12a, 12b, to the approximated position. When the electrical circuit is closed, or completed, actuator 90 is operable to activate, or supply energy to jaw members 110, 120. More specifically, as shaft members 12a, 12b are moved to the approximated position about finger ring 43, electrical contacts 52a, 52b, of finger ring 43 are urged into contact with respective electrical contacts 53a, 53b of shaft members 12a, 12b, respectively, to complete, or close the circuit, thus allowing activation of actuator 90 to supply energy to jaw members 110, 120. In other words, electrical contacts 52a, 52b and corresponding electrical contacts 53a, 53b permit activation of actuator 90 only when jaw members 110, 120 are disposed in the closed position, e.g., when contacts 52a and 53a and contacts 52b and 53b are in electrical contact with one another. Such a safety feature helps prevent inadvertent energization of forceps 10, e.g., when jaw members 110, 120 are not disposed in the closed position.

Alternatively, as opposed to point contacts 52a, 52b, 53a, 53b, shown in FIGS. 8A-8B, finger ring 43 and shaft members 12a, 12b may include slide contacts (not explicitly shown), or any other suitable electrical or electro-mechanical connections that inhibit activation of actuator 90 when jaw members 110, 120 are disposed in the open position. Further, rather than completing an electrical circuit upon contact, contacts 52a, 52b of finger ring 43 and electrical contacts 53a, 53b of tracks 22a, 22b of shaft members 12a, 12b, respectively, may be pressure-sensitive contacts. In such an embodiment, activation of actuator 90 is inhibited until a specific minimum pressure between contacts 52a and 53a and/or between contacts 52b, 53b is achieved, e.g., until shaft members 12a, 12b are moved into approximation about finger ring 43 to exert a specific minimum pressure on finger ring 43. As discussed above, the relative approximation of shaft members 12a, 12b effects both the gap distance "g" between jaw members 110, 120 and the closure pressure between jaw members 110, 120. Thus, the pressure-sensitive contacts may be used to inhibit activation of actuator 90 until a desired gap distance "g" and/or closure pressure between jaw members 110, 120 is achieved. As mentioned above, the gap distance "g" preferably falls within a range of about 0.001 inches to about 0.006 includes with the closure pressure in the range of about 3 kg/cm$^2$ to about 16 kg/cm$^2$.

Referring now to FIGS. 6A-6B, once tissue grasped between jaw members 110, 120 has been sealed, or where only tissue division is desired, knife assembly 40 may be advanced from the retracted position (FIG. 6A) to the extended position (FIG. 6B) to cut tissue grasped between jaw members 110, 120. More particularly, when it is desired to cut tissue grasped between jaw members 110, 120, the user may insert a finger through finger ring 43 of knife assembly 40 and translate finger ring 43 distally such that knife bar 45 is advanced through blade channels 114, 124 of jaw members 110, 120, allowing distal cutting edge 46 to be translated through tissue grasped between jaw members 110, 120. As finger ring 43 is translated distally, pivot 103 is translated proximally through slot 47 defined within knife bar 45. Longitudinal tracks 22a, 22b defined within handle portions 18a, 18b of shaft members 12a, 12b, respectively, guide the translation of knife assembly 40 between the retracted and extended positions. In particular, tracks 22a, 22b inhibit eccentric movement of knife bar 45 through knife channels 114, 124 of jaw members 110, 120, respectively, as knife assembly 40 is translated relative to jaw members 110, 120, thereby reducing the likelihood of blade splay and allowing for a relatively easy translation of distal cutting edge 46 of knife bar 45 through tissue. Translation of knife bar 45 through knife channels 114, 124 may also be facilitated by the configuration of knife bar 45, e.g., the configuration of knife bars 45a-45d and corresponding knife channels 114, 124, discussed above with reference to FIGS. 7A-7D.

Forceps 10 may also include a knife lock feature (not explicitly shown) configured to inhibit deployment of knife bar 45 when jaw members 110, 120 are disposed in the open position and/or configured to inhibit movement of jaw members 110, 120 to the open position when knife bar 45 is disposed in the extended position. In the embodiments of FIGS. 7A and 7C, discussed above, knife bars 45, 45c are inhibited from being deployed, e.g., from the retracted position to the extended position, when jaw members 110, 120 are disposed in the open position due to the configuration of knife bars 45a, 45c and corresponding blade channels 114a, 124a and 114c, 124c, respectively. In other words, only when jaw members 110, 120 are in the closed position are flanges 49a, 49c aligned with blade channels 114a, 124a and 114c, 124c, respectively, to permit translation of knife bars 45a, 45c, respectively, therethrough. When jaw members 110, 120 are in the open position, translation of knife bars 45a, 45c is inhibited. Similarly, when knife bars 45a, 45c are disposed in the extended position, jaw members 110, 120 are inhibited from being moved to the open position due to the engagement of flanges 49a, 49c within respective blade channels 114a, 124a and 114c, 124c. However, in these embodiments, or in any other embodiment, shaft members 12a, 12b and/or jaw members 110, 120 of forceps 10 may additionally, or alternatively, include specific features configured to inhibit advancement of knife bar 45 when jaw members 110, 120 are disposed in the open position. For example, commonly-owned U.S. Pat. No. 7,252,667 to Moses et al., the entire disclosure of which is hereby incorporated by reference herein, discloses a safety lockout mechanism that prevents advancement of the cutting mechanism until the jaw members are moved to the closed position. The safety lockout mechanism is automatically disengaged upon movement of the jaw members to the closed position to permit advancement of the cutting mechanism, e.g., from the retracted position to the extended position.

Once tissue has been sealed and divided, finger ring 43 may be translated proximally back to the retracted position, as shown in FIG. 6A. Thereafter, shaft members 12a, 12b may be moved apart from one another to the open position such that jaw members 110, 120 are moved to the spaced-apart position. Forceps 10 may then be removed from the surgical site.

Referring now to FIGS. 9A-9B, another embodiment of a finger ring 143 configured for use with forceps 10 is shown. Finger ring 143 is similar to finger ring 43 (see FIG. 4), discussed above, except that finger ring 143 is formed from a resiliently compressible material, e.g., silicon or any other suitable polymer. Compressible finger ring 143 assures a constant closing pressure between jaw members 110, 120 during approximation of shaft members 12a, 12b. More specifically, finger ring 143 may be configured to uniformly and consistently compress from an initial state having a first diameter "d" (FIG. 9A) to a compressed state having a second diameter "d'" (FIG. 9B), that is smaller than diameter "d," upon movement of shaft members 12a, 12b to the closed position to thereby regulate the closing pressure of jaw members 110, 120.

With continued reference to FIGS. 9A-9B, when shaft members 12a, 12b are moved to the closed position compressing finger ring 143 therebetween, finger ring 143 is disposed in the compressed state wherein finger ring 143 defines second diameter "d'." In other words, in this position, shaft members 12a, 12b are spaced apart by the second diameter "d'" and, accordingly, jaw members 110, 120 are separated by the desired minimum gap distance "g" (see FIG. 2). Second diameter "d'" may thus be selected in accordance with the desired minimum gap distance "g" (see FIG. 2) between jaw members 110, 120, respectively, similarly as discussed above. Further, the material(s) comprising finger ring 143 may be selected to achieve a desired compressibility. More particularly, where a greater closing pressure between jaw members 110, 120 is desired, a finger ring 143 including a relatively more-compressible material may be chosen. On the other hand, where a smaller closing pressure is desired a relatively more-compressible material may be chosen. Alternatively, the material may be selected to achieve a particular closure pressure between jaw members 110, 120 that falls within a desired range, e.g., from about 3 kg/cm$^2$ to about 16 kg/cm$^2$.

As discussed above, each shaft member 12a, 12b, including jaw members 120, 110, respectively, may be formed as a single component, e.g., via stamping. The relatively inexpensive and simplistic stamping process allows for a reduced overall cost in manufacture of shaft members 12a, 12b. Knife bar 45 may also be formed from stamping. Dip coating, or otherwise insulating handle portions 18a, 18b of shaft members 12a, 12b and molding (or dip coating) handle portion 42 of knife assembly 40 are also relatively simple and inexpensive processes. Further, since knife assembly 40 defines the gap distance "g" between jaw members 110, 120, the need for providing other gap setting features is obviated. Put more generally, forceps 10 provides a relatively inexpensive device to manufacture, while still being capable of effectively grasping, sealing, and/or dividing tissue.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A forceps, comprising:
   first and second jaw members;
   first and second handles operably coupled to the first and second jaw members such that at least one of the first or second handles is moveable relative to the other between an open position and a closed position for moving the first and second jaw members between a spaced-apart position and an approximated position, wherein the first and second handles are monolithically formed with the respective first and second jaw members; and
   a knife including a finger handle disposed between the first and second handles, the finger handle configured to block further closure of the first and second handles beyond the closed position of the first and second handles, thereby defining a minimum gap distance between the first and second jaw members, the knife longitudinally translatable along a longitudinal axis defined between the first and second jaw members between a retracted position in which the knife is disposed proximal of the first and second jaw members and an extended position in which the knife is at least partially disposed within at least one of the first or second jaw members.

2. The forceps according to claim 1, wherein the minimum gap distance between the first and second jaw members is in the range of 0.001 inches to 0.006 inches.

3. The forceps according to claim 1, wherein at least one of the first and second jaw members is adapted to connect to a source of electrosurgical energy.

4. The forceps according to claim 1, wherein at least one of the first or second jaw members includes a longitudinally-extending knife channel defined therein, the longitudinally-extending knife channel configured to permit reciprocation of the knife therethrough.

5. The forceps according to claim 1, wherein the knife includes a slot defined therein, the slot configured to receive a pivot pin therethrough upon which the first and second jaw members are pivotably coupled, the pivot pin configured to translate along the slot as the knife is translated between the retracted position and the extended position.

6. A forceps, comprising:
   first and second jaw members;
   first and second handles operably coupled to the first and second jaw members such that at least one of the first or second handles is moveable relative to the other between an open position and a closed position for moving the first and second jaw members between a spaced-apart position and an approximated position, the first and second handles defining respective first and second troughs, wherein each handle and its respective jaw member are monolithically formed as a single component; and
   a knife including a finger handle, at least a portion of the finger handle disposed within each of the first and second troughs, the first and second troughs configured to guide longitudinal translation of the knife in a direction along a longitudinal axis of the forceps defined between the first and second jaw members between a retracted position in which the knife is proximal of the first and second jaw members and an extended position in which the knife is at least partially disposed within at least one of the first or second jaw members.

7. The forceps according to claim 6, wherein, in the extended position, the knife extends between the first and second jaw members.

8. The forceps according to claim 6, wherein the finger handle of the knife and the troughs of the first and second handles define complementary transverse, cross-sectional configurations to facilitate translation of the knife between the retracted position and the extended position.

9. The forceps according to claim 6, wherein at least one of the first and second jaw members is adapted to connect to a source of electrosurgical energy.

10. The forceps according to claim 6, wherein at least one of the first and second jaw members includes a longitudinally-extending knife channel defined therein, the longitudinally-extending knife channel configured to permit reciprocation of the knife therethrough.

11. The forceps according to claim 6, wherein the finger handle includes at least one contact that is configured to engage at least one corresponding contact disposed within the trough of at least one of the first and second handles to close an electrical circuit upon movement of the first and second jaw members to the approximated position.

12. The forceps according to claim 6, wherein the finger handle includes at least one pressure contact configured to engage at least one corresponding pressure contact disposed within the trough of at least one of the first and second handles to close an electrical circuit between the first and second jaw members upon exertion of a pre-determined pressure between the at least one pressure contact of the finger handle and the at least one corresponding pressure contact disposed within the trough of at least one of the first and second handles.

13. A forceps, comprising:
   first and second jaw members;
   first and second handles operably coupled to the first and second jaw members such that at least one of the first or second handles is moveable relative to the other between an open position and a closed position for moving the first and second jaw members between a spaced-apart position and an approximated position, each of the first and second handles having a pair of sidewalls that extend in a direction along a longitudinal axis of the forceps to define respective first and second troughs therebetween, each of the first and second handles having a base that extends in a direction transverse to the longitudinal axis from a first sidewall of the pair of sidewalls to a second sidewall of the pair of sidewalls to interconnect the pair of sidewalls; and a knife including a finger handle having a first diameter, the finger handle disposed between the first and second handles, at least a portion of the finger handle disposed within each of the troughs of the first and second handles, the finger handle configured to contact the base of each of the first and second troughs such that the finger handle is compressible from the first diameter to a second diameter to define a minimum gap distance between the jaw members when the jaw members are disposed in the approximated position, the troughs further configured for guiding translation of the knife between a retracted position and an extended position.

14. The forceps according to claim 13, wherein at least one of the first and second jaw members is adapted to connect to a source of electrosurgical energy.

15. The forceps according to claim 13, wherein the minimum gap distance between the first and second jaw members is in the range of about 0.001 inches to about 0.006 inches.

16. The forceps according to claim 13, wherein at least one of the first and second jaw members includes a longitudinally-extending knife channel defined therein, the longitudinally-extending knife channel configured to permit reciprocation of the knife therethrough.

17. The forceps according to claim 13, wherein the finger handle of the knife and the troughs define complementary transverse, cross-sectional configurations to facilitate translation of the knife between the retracted position and the extended position.

18. The forceps according to claim 13, wherein the troughs are configured for guiding translation of the entire finger handle along the longitudinal axis such that the knife is translated between the retracted position and the extended position.

* * * * *